United States Patent
Oehy et al.

[11] Patent Number: 5,911,758
[45] Date of Patent: *Jun. 15, 1999

[54] TIBIA PLATFORM FOR A KNEE JOINT PROSTHESIS AND KNEE JOINT PROSTHESIS WITH SUCH A TIBIA PLATFORM

[75] Inventors: Jürg Oehy; Kurt Bider, both of Winterthur; Martin Schoch, Stallikon, all of Switzerland; Wolfgang Schwägerl, Wien; Nikolaus Böhler, Linz, both of Austria

[73] Assignee: Sulzer Orthopaedie AG, Baar, Switzerland

[ * ] Notice: This patent is subject to a terminal disclaimer.

[21] Appl. No.: 08/667,922

[22] Filed: Jun. 20, 1996

[30] Foreign Application Priority Data

Jun. 21, 1995 [EP] European Pat. Off. ............ 95810417

[51] Int. Cl.$^6$ ........................................ A61F 2/38
[52] U.S. Cl. .............................. 623/20; 623/22
[58] Field of Search ................ 623/22, 23, 20, 623/16, 18

[56] References Cited

U.S. PATENT DOCUMENTS

| | | |
|---|---|---|
| 4,388,921 | 6/1983 | Sutter et al. .......................... 606/71 |
| 4,484,570 | 11/1984 | Sutter et al. .......................... 606/71 |
| 5,019,103 | 5/1991 | Van Zile . |
| 5,074,879 | 12/1991 | Pappas et al. ......................... 623/23 |
| 5,246,459 | 9/1993 | Elias ...................................... 623/20 |
| 5,330,535 | 7/1994 | Moser et al. .......................... 623/20 |

FOREIGN PATENT DOCUMENTS

| | | |
|---|---|---|
| 0 170 779 | 2/1986 | European Pat. Off. . |
| 0 495 340 | 7/1992 | European Pat. Off. . |
| 0 502 815 | 9/1992 | European Pat. Off. . |
| 1057763 | 2/1967 | United Kingdom . |

*Primary Examiner*—Michael J. Milano
*Assistant Examiner*—Tram Anh T. Nguyen
*Attorney, Agent, or Firm*—Townsend and Townsend and Crew LLP

[57] ABSTRACT

The tibia platform (1) contains a joint support (5) and an anchoring part (4) with passage openings (12) for fastening elements (14) for fastening the anchoring part (4) to the tibia bone (3). The passage openings (12) are each executed with a femur-side, upper countersink (25). At least one passage opening (12) not used for the fastening is provided with a closure plug (15) which can be inserted from above, which is executed with a supporting surface (16a) running around this sealing surface (16a) and can be braced in the countersink (25). The closure plug (15) contains a number of spring tongues (18) which can be introduced into the relevant passage opening (12) and which form a snap connection with the wall of the passage opening (12), and a central cylindrical protusion (17) which is provided with a blind bore (17a) open upwards for receiving a setting tool (20). In this manner a secure sealing of the passage opening (12) is attained and the movement into the tibia bone bed of abraded particles possibly originating between the anchoring part (4) and the joint support (5) is prevented.

8 Claims, 1 Drawing Sheet

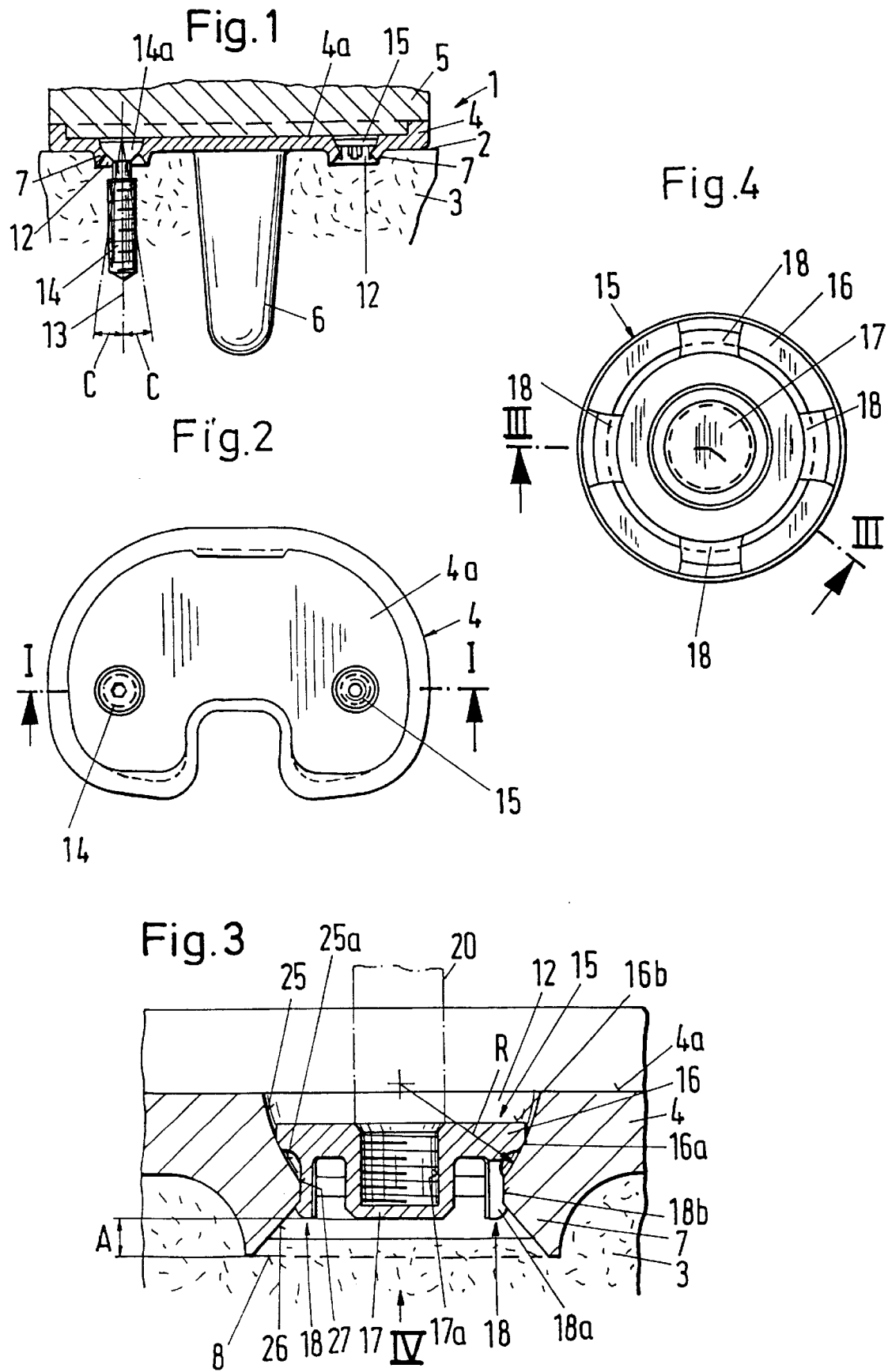

TIBIA PLATFORM FOR A KNEE JOINT PROSTHESIS AND KNEE JOINT PROSTHESIS WITH SUCH A TIBIA PLATFORM

The invention relates to a tibia platform and in particular to a closure plug for fastening over unused passage openings for a knee joint prothesis when the knee joint prothesis is fastened to a tibia bone.

BACKGROUND OF THE INVENTION

Furthermore the invention relates to a knee joint prosthesis executed with such a tibia platform as well as a closure plug for such a tibia platform.

A tibia platform of the type named which is known from FR-A-2 653 992 contains a metallic anchoring part and a joint support of polyethylene which can be inserted into this anchoring part. The anchoring part is executed with projections which can be introduced into the tibia bone in the form of a central pin and two ring shaped protrusions, the latter each containing a passage opening for receiving a dowel-like holder element or a clamping part with an inclined guide bore for a bone screw. For the guidance of the bone screws, which mainly serve to secure the anchoring part against rotation on a resection plane of the tibia, relatively voluminous bores are thus required for receiving the dowel and the clamping part, which can weaken the tibia bone. If for any reason, e.g. due to the state of the tibia bone tissue, the use of one or the other of the bone screws is dispensed with, abrasion of plastic and hence a direct contact between the plastic of the joint support and the tibia bone tissue may result—by cold flow of the plastic of the joint support in the region of the passage opening or passage openings not used in the particular case.

SUMMARY OF THE INVENTION

The object of the invention is to provide a tibia platform improved in particular in this respect, which permits a simple adaptation of the fastening arrangement to the given anatomical conditions with low cost and complexity during preparation of the tibia bone, and which at the same time ensures a secure screening of the bone tissue against undesired contact with abraded particles.

This object is satisfied a closure plug for insertion from the femur side to an anchoring part fastened to the tibia.

The anchoring part of this invention is capable of receiving one or more closure plugs at passage openings. Each closure plug is associated with one of the passage openings when that passage opening does not have fastener elements. This arrangement permits an intentional and controllable local screening of an opening from the bone tissue of the tibia which is located in the vicinity of an unused passage opening. The closure plug executed in accordance with the invention is relatively simple to manufacture, and a large supply of closure plugs can be kept available which can be inserted into or removed from the respective free passage opening by the surgeon. The embodiment in accordance with the invention permits in particular a sealing off of the passage openings at an advantageously early phase of the operation, e.g. before or immediately after the placement of the anchoring part onto the resection surface of the tibia bone, independently of the form and the attachment of the joint support. A further advantage consists in the fact that identically constructed anchoring parts are applicable for cementless implantation as well as for implantation using bone cement. In the latter application in particular the passage openings located in the region of the bone cement are screened off by the closure plugs and thus a contact between the bone cement and the joint support is prevented. The anchoring part equipped in accordance with the invention further permits the use of an advantageously simply executed joint support in a design completely independent of the arrangement of the closure plugs.

BRIEF DESCRIPTION OF THE DRAWING

A closure plug for a tibia platform in accordance with the invention is the subject of claim 9.

The invention will be explained on the basis of an exemplary embodiment schematically represented in the drawings. Shown are:

FIG. 1 illustrates parts of a knee joint prosthesis executed in accordance with the invention with a tibia platform in a section corresponding to line I—I in FIG. 2, FIG. 2 illustrates a part of the tibia platform of FIG. 1 in a plan view, FIG. 3 illustrates a detail of the tibia platform of FIG. 1 in a larger representation, with a closure plug in a section corresponding to the line III—III in FIG. 4, FIG. 4 illustrates the closure plug of FIG. 2 in a bottom view along arrow IV in FIG. 3.

DESCRIPTION OF THE PREFERRED EMBODIMENT

The knee joint prosthesis in FIGS. 1 and 2 contains a tibia platform 1 and an anchoring part 4 of metal, e.g. titanium, which can be placed onto a resection surface 2 of tibia bone 3 and which surrounds a joint support 5 of a plastic, e.g. polyethylene, which can be placed upon a supporting surface 4a of the anchoring part 4 and can be latched to this anchoring part 4. The anchoring part 4 is executed with a central pin 6 which can be introduced into a recess of the tibia bone 3 and with two annular projections 7 which can be introduced into corresponding recesses of the tibia bone 3, each projection 7 being provided with a passage opening 12 passing through the anchoring part 4. The passage openings 12 are each suitable for or provided for receiving a fastening element 14 of an arbitrary type which can be anchored in the tibia bone 3, and which is shown in the form of a bone screw which can be screwed into the bone tissue. In the example shown a single fastening element 14 is provided for fastening the anchoring part 4 at the tibia bone 3 and serves principally for the primary stable fastening of the anchoring part 4 at the resection surface 2. The passage opening 12 not used for the fastening of the anchoring part 4 is provided with a closure plug 15 which can be inserted and fixed from above, from the femur side.

In accordance with a different embodiment which is not shown, the anchoring part 4 can be provided with several, e.g. four, passage openings 12; and two or more, e.g. three, corresponding fastening elements 14 can be provided, where the unused passage openings 12 free of fastening elements 14 are each likewise provided with one closure plug 15. An embodiment is also possible in which the provision of a fastening element 14 is dispensed with and all passage openings 12 are provided with closure plugs 15.

In accordance with the representation of FIGS. 1 and 3 the passage openings 12 are each executed with a femur-side, upper countersink 25 and a tibia-side, lower countersink 26, which together with the upper countersink 25 bounds a locally narrowed peripheral part 27 of the passage opening 12, and with the tibia-side, lower end section of the projection 7 bounds an edge part 8 in the form of a cutting edge which can be introduced into the bone bed. As seen in particular in FIG. 2, the upper countersinks 25 of the passage openings 12 can each have the form of a dome, which is defined by a conical upper end section and an at least approximately spherical supporting surface 25a formed between this end section and the peripheral part 27. The supporting surfaces 25a are shown in FIG. 3 to be executed each with a radius R. In accordance with FIG. 1 the fastening elements 14 can each be executed with a head part 14a which has a corresponding convex placement surface which can be placed on the concave supporting surface 25a and which correspondingly permits the attachment of the fastening element 14 to the bone tissue 1 in an angular position in each case which corresponds to that of the axis 13 of the passage opening 12 or which deviates from this axis 13 by an angle C indicated in FIG. 1. The embodiment represented thus permits a corresponding adaptation to the given anatomical conditions variable within this angular range.

The closure plug 15 contains a plate-like sealing part 16 which can be introduced so that it is sunk into the upper countersink 25 of the respectively non-used passage opening 12, a central hat-like raised portion or upward cylindrical 17 projecting therefrom towards the tibia side of the anchoring part 4 and a number of spring tongues 18 [four in the drawing] arranged in segment-like manner projecting from one boundary part of the sealing part 16 toward the tibia side of the anchoring part 4. The sealing part 16 is executed with a sealing surface 16a running about its periphery which can be placed on a wall part of the countersink 25, shown on the supporting surface 25a. The closure plug 15 is held in the passage opening 12 by the spring tongues 18 and its sealing surface 16a is pressed against the supporting surface 25a.

As seen in particular in FIG. 3, the sealing surface 16a can be formed by a conical countersurface of the sealing part 16 corresponding to one of the supporting surfaces 25a, which sealing part 16 co-operates with the supporting surface 25a via an annular contact surface and thus ensures an effective sealing of the passage opening 12. The raised portion 17 is executed with a blind bore 17a open towards the femur side of the anchoring part 4 in its snapped-in position, which can be provided with a thread as shown and is provided to receive a follower part of a setting tool 20 indicated by the chain dotted line. The spring tongues 18 are formed of elastically deformable lug-like wall segments interrupted elastic cylindrical segments protruding outwards from the boundary region of the sealing part 16 and movable with respect to one another. Each wall segment has an end section 18a which can be introduced into the lower countersink 26 and braced against the wall of this countersink 26 and a recess 18b corresponding to the narrowed peripheral part 27 of the passage opening 12 and accommodating this latter. As shown the closure plug 15 is executed in such a manner that it is held in the passage opening 12 at a distance A from the boundary part 8, which permits a penetration of this boundary part 8 into the bone bed by a corresponding amount.

The closure plug 15, which can consist of the same material as the anchoring part 4, e.g. of a titanium alloy, can in each case be introduced into the passage opening 12 by the setting tool 20, where the spring tongues 18 are elastically deformed during the transition of the end parts 18a over the peripheral part 27 and subsequently form a snap connection with the wall of the passage opening 12, by means of which the sealing part 16 of the sealing surface 16a is braced against the supporting surface 25a and thereby the part of the bone tissue 1 located in the region of the passage opening 12 is sealed off from the femur side of the anchoring part 4 and a passage of abraded particles of the joint support 5 is prevented. The closure plug 15 can be inserted via the setting tool 20 in a simple manner into the passage opening 12 and removed therefrom. The embodiment of the closure plug 15 described enables a secure sealing of the passage opening 12 even for relatively thin anchoring parts 4, e.g. such anchoring parts 4 with wall thicknesses of 4 to 5 mm, which are as a rule not suitable for threading.

Numerous embodiments of the invention are possible. In contrast to the representation in FIG. 3 the closure plug 15 can be executed in such a manner that its femur-side surface 16b lies essentially flush with the supporting surface 4a of the anchoring part 4 in its snapped-in position, whereby a cold flow of the plastic of the joint support 5 in this region can be prevented. Correspondingly the closure plug 15 can be executed with a larger height dimension and/or with a thicker sealing part 16. The sealing part 16 can also be executed with a differently formed, e.g. cylindrical or spherical, sealing surface 16a, which can be provided for cooperating with the supporting surface 25a or with the conical end section 25 of the countersink. In accordance with an embodiment not shown the upper countersinks of the passage openings 12 can each be executed conically over their entire depth and be provided for receiving a correspondingly conical head part of a fastening element or of a sleeve, which can receive a fastening element that can be placed in different angular positions. With such an embodiment the closure plugs 15 can be executed with conical sealing surfaces which can also be placed aerially so as to space the conical sealing surfaces apart the countersinks 25 or, if desired, with sealing surfaces that can be placed with line contact, e.g. cylindrical sealing surfaces. In place of the screw connection shown between the raised portion 17 and the setting tool 20 a different follower connection, e.g. a disengageable hook connection or the like, can be provided. It is furthermore clear that corresponding closure plugs can also be provided each with a differing number of spring tongues 18 from that shown in the illustrated arrangement, e.g. three, six, eight or more.

In summary the invention can be described as follows:

The tibia platform contains a joint support 5 and an anchoring part 4 with passage openings 12 for fastening elements 14 for fastening the anchoring part 4 to the tibia bone 3. The passage openings 12 are each executed with a femur-side, upper countersink 25. At least one passage opening 12 not used for the fastening is provided with a closure plug 15 which can be inserted from above, which is executed with a supporting surface 16a running around this sealing surface 16a and can be braced in the countersink 25. The closure plug 15 contains a number of spring tongues 18 which can be introduced into the relevant passage opening 12 and which form a snap connection with the wall of the passage opening 12, and a hat-like central raised part or cylindrical protrusion 17 which is provided with a blind bore 17a open upwards for receiving a setting tool 20. A secure sealing of the passage opening 12 is thereby attained and the movement into the tibia bone bed of abraded particles possibly originating between the anchoring part 4 and the joint support 5 is prevented.

We claim:

1. A closure plug for fastening over unused passage openings for a knee joint prosthesis fastened to a tibia bone wherein the knee joint prosthesis includes, an anchoring part, a plurality of passage openings defined in the anchoring part for receiving a fastening element for fastening the anchoring part into the tibia bone on a tibia side of the anchoring part, the anchoring part at each of the passage openings constructed with a countersink defining a recessed receptacle surrounding the passage openings on a femur side of the anchoring part, the closure plug for one of the plurality of openings comprising:

a closure plug for insertion from the femur side;

a sealing surface defined at a top of the closure plug which can be inserted in the countersink so as to seat at the recessed receptacle around the countersink to seal off the passage opening; and, a plurality of spring tongues which can be inserted into the passage openings having interfering snap connections with a wall of the passage opening for holding the closure plug to the countersink when the countersink is not occupied by a fastening element.

2. A closure plug for fastening over unused passage openings for a knee joint prosthesis according to claim 1 and wherein:

the closure plug has a cylindrical central raised portion placed at a distance from the spring tongues protruding from the tibia side of the anchoring part; and, the cylindrical central raised portion defines a blind bore open towards the femur side for receiving a setting tool.

3. A closure plug for fastening over unused passage openings for a knee joint prosthesis according to claim 2 and wherein:

the blind bore is provided with threading.

4. A closure plug for fastening over unused passage openings for a knee joint prosthesis according to claim 1 and wherein:

the spring tongues are formed of lug-like wall sections protruding from the sealing surface toward the tibia side and moveable relative to one another.

5. A knee joint prosthesis adapted to be fastened to a tibia bone comprising:

an anchoring part fastened to a body of the knee joint prosthesis;

a plurality of passage openings defined in the anchoring part for receiving a fastening element for fastening the anchoring part into the tibia bone, at least one fastening element for fastening the anchoring part of the knee joint prosthesis to the tibia bone;

the anchoring part at the passage openings constructed with a first countersink defining a recessed receptacle surrounding the passage openings on a femur side of the anchoring part opening to a tibia side of the anchoring part;

at least one closure plug for insertion from the femur side;

a sealing surface defined at a top of the closure plug which can be inserted in the countersink so as to seat at the recessed receptacle around the countersink to seal off the passage opening; and, a plurality of spring tongues which can be inserted into the passage openings having interfering snap connections with a wall of the passage opening for holding the closure plug to the countersink when the countersink is not occupied by a fastening element.

6. A knee joint prosthesis is adapted to be fastened to a tibia bone according to claim 5 further comprising:

the recessed receptacle has a form of a dome with a spherical surface; and, the closure plug has a form of a dome with a corresponding spherical surface.

7. A knee joint prosthesis adapted to be fastened to a tibia bone according to claim 5 further comprising:

each of the passage openings of the anchoring part is constructed with a second countersink formed at the tibia side of the anchoring part so as to define with the first countersink a locally narrowed peripheral part of the passage opening;

the spring tongues of the closure plug are each constructed with an end section which can be inserted into the second countersink with a depression corresponding to the narrowed peripheral part.

8. A knee joint prosthesis adapted to be fastened to a tibia bone according to claim 5 further comprising:

the passage openings are formed with a tibia side protrusion from the anchoring part for introduction to the tibia bone;

the tibia side protrusion bounds an edge portion of the passage openings in a manner of a cutting edge; and, the closure plug is configured to be held at a distance from this edge portion to allow penetration of the edge portion into the tibia bone.

* * * * *